United States Patent [19]

Yamashita et al.

[11] Patent Number: 5,412,106
[45] Date of Patent: May 2, 1995

[54] PROCESS FOR PRODUCTION OF 2-THIOPHENE ALDEHYDES

[75] Inventors: Kazuyoshi Yamashita, Hyogo; Kenji Saito, Hirakata; Shinzo Seko, Toyonaka, all of Japan

[73] Assignees: Sumitomo Chemical Co., Ltd., Osaka; Sumitomo Seika Chemicals Co., Hyogo, both of Japan

[21] Appl. No.: 137,790

[22] Filed: Oct. 19, 1993

[30] Foreign Application Priority Data

Oct. 29, 1992 [JP] Japan .................................. 4-291193

[51] Int. Cl.$^6$ .......................................... C07P 333/24
[52] U.S. Cl. ............................................... 549/70
[58] Field of Search ............................................ 549/70

[56] References Cited

U.S. PATENT DOCUMENTS

| 2,601,479 | 6/1952 | Weston, I | 549/70 |
| 2,741,622 | 4/1956 | Brackmeyer et al. | 549/70 |
| 2,853,493 | 9/1958 | Weston, II | 549/70 |
| 3,576,822 | 4/1971 | Edie et al. | 549/70 |
| 4,321,399 | 3/1982 | Jones et al. | 549/70 |

FOREIGN PATENT DOCUMENTS

| 0095340 | 5/1983 | European Pat. Off. . |
| 0248393 | 6/1987 | European Pat. Off. . |
| 0557834 | 2/1993 | European Pat. Off. . |
| 56-133220 | 10/1981 | Japan | 549/70 |

OTHER PUBLICATIONS

Fieser et al, "Reagents For Organic Synthesis", John Wiley & Sons, pp. 284 (1967).
Chadwick et al. (1973) *J.C.S. Perkin I*: 2327–32.

*Primary Examiner*—James H. Reamer
*Attorney, Agent, or Firm*—Birch, Stewart, Kolasch & Birch

[57] ABSTRACT

There is disclosed a process for the production of 2-thiophene aldehydes, in which the 2-thiophene aldehydes are obtained by the formylation of thiophene or derivatives thereof with formamides and phosgene.

3 Claims, No Drawings

PROCESS FOR PRODUCTION OF 2-THIOPHENE ALDEHYDES

FIELD OF THE INVENTION

The present invention relates to a process for the production of 2-thiophene aldehydes that are important compounds as intermediates for use in the synthesis of medicaments, agricultural chemicals, and the like.

BACKGROUND OF THE INVENTION

As the process for the production of 2-thiophene aldehydes, there have hitherto been known various processes; for example, 2-thiophene aldehydes are obtained by the Vilsmeier reaction using formamides and phosphorous oxychloride (see, e.g., U.S. Pat. No. 2,853,493), or formamides and acid chlorides such as phosphorous oxychloride are used under the presence of pyridine (see, e.g., JP-A 56-133220).

In the Vilsmeier reaction using phosphorous oxychloride, however, when thiophene derivatives each having a substituent at the 3rd position thereof are used, a mixture of the 2-formyl product and the 4-formyl product at a ratio of 4:1 is formed with the percent yield of the 2-formyl product being only about 33%; therefore, for the purpose of obtaining 2-thiophene aldehydes, such a mixture of the products should be separated (see, e.g., J. Chem. Soc. Perkin Trans I, 1973, 2327). In addition, these conventional processes have disadvantages in that they lead to the formation of phosphorous-containing waste water of great volume and that it is necessary to recover pyridine which is then to be converted into anhydrous pyridine; therefore, they are not always satisfactory from an industrial point of view.

SUMMARY OF THE INVENTION

Under these circumstances, the present inventors have intensively studied the production of 2-thiophene aldehydes. As the result, they have found that 2-thiophene aldehydes can be produced at high yield from thiophene or derivatives thereof and formamides by using phosgene in place of phosphorous oxychloride or pyridine, and in particular, 2-formyl products can be selectively obtained from thiophene derivatives each having a substituent at the 3rd position thereof, thereby completing the present invention.

Thus, the present invention provides a process for the production of 2-thiophene aldehydes, characterized in that these aldehydes are obtained by the formylation of thiophene or derivatives thereof with formamides and phosgene.

DETAILED DESCRIPTION OF THE INVENTION

The production process of the present invention is based on the novel finding that the formylation of thiophene or derivatives thereof with formamides and phosgene gives 2-thiophene aldehydes in high yield.

Examples of the formamide are N,N-dimethylformamide, N,N-diethylformamide, N-methylformamide, N-ethylformamide, N-phenyl-N-methylformamide, and morpholinylformamide. Among these formamides, preferably used is N,N-dimethylformamide.

The formamide is usually used in an amount of 1 to 10 equivalents, preferably 1 to 2 equivalents, to one equivalent of thiophene or derivative thereof. As the case may be, the formamide may be used as a solvent within the above-mentioned range.

The phosgene is usually used in an amount of 1 to 10 equivalents, preferably 1 to 2 equivalents, to one equivalent of thiophene or derivative thereof.

Not only thiophene but also various thiophene derivatives can be used in the reaction, examples of which are alkyl-substituted thiophene derivatives such as 2-methylthiophene, 2-t-butylthiophene, 2-cyclopropylthiophene, 3-methylthiophene, 3-t-butylthiophene, 3-cyclopropylthiophene, and 2,3-dimethylthiophene; aromatic-substituted thiophene derivatives such as 2-arylthiophene derivatives (e.g., 2-phenylthiophene) and 3-arylthiophene derivatives (e.g., 3-phenylthiophene); lower alkoxy-substituted thiophene derivatives such as 2-methoxythiophene and 3-methoxythiophene; halogen-substituted thiophene derivatives such as 2-chlorothiophene, 2-bromothiophene, 3-chlorothiophene, and 3-bromothiophene; dialkylamino-substituted thiophene derivatives such as 2-dimethylaminothiophene and 3-dimethylaminothiophene; acylamino-substituted thiophene derivatives such as 2-acetoaminothiophene and 3-acetoaminothiophene; and carboxyl- or lower alkoxycarbonyl-substituted thiophene derivatives such as 2-carboxythiophene, 3-carboxythiophene, 2-methoxycarbonylthiophene, and 3-methoxycarbonylthiophene.

According to the production process of the present invention, 2-thiophene aldehydes can be produced with excellent selectivity for the position of substituent groups. For example, when thiophene derivatives each having a substituent group at the 2nd position thereof are used in the reaction, 2-thiophene aldehydes each having the substituent group at the 5th position thereof are obtained. When thiophene derivatives each having a substituent group at the 3rd position thereof are used in the reaction, 2-thiophene aldehydes each having the substituent group at the 3rd position thereof are obtained. Also when thiophene derivatives each having substituent groups at the 2nd and 3rd positions thereof are used in the reaction, 2-thiophene aldehydes each having the substituent groups at the 4th and 5th positions thereof are obtained.

In usual cases, phosgene gas, liquid phosgene, or a solution of phosgene is introduced into an organic solvent containing, together with a formamide, thiophene or a derivative thereof. Alternatively, an organic solvent containing, together with a formamide, thiophene or a derivative thereof may be added to liquid phosgene or a solution of phosgene.

The reaction is preferably performed in an organic solvent, although it is not always necessary to use any solvent therefor. Examples of the organic solvent which can be used in the reaction are aliphatic hydrocarbons such as hexane and heptane; organic chlorinated hydrocarbons such as methylene chloride, chloroform, 1,1,-dichloroethane, 1,2-dichloroethane, 1,1,2-trichloroethane, 1,1,2,2-tetrachloroethane, trichloroethylene, and perchloroethylene; acetonitrile, dialkylethers, and the like.

The reaction is usually performed at a temperature of 0° C. to 95° C., preferably 40° C. to 90° C. When the temperature is lower than 0° C., the reaction rate is quite slow. When the temperature exceeds 95° C., the reaction mixture tends to change into a tar-like form, thereby causing a reduction in the yield of 2-thiophene aldehydes. The temperatures lower than 0° C. or higher than 95° C. are not preferred for the production process of the present invention.

After completion of the reaction, the Vilsmeier reaction intermediate formed in the reaction mixture is hydrolyzed under ordinary conditions known in the art to give the desired 2-thiophene aldehyde. The hydrolysis is effected by the addition of water or aqueous ammonium chloride to the reaction mixture, or by the addition to the reaction mixture, of a solution of an alkali salt, such as sodium hydroxide, sodium carbonate, or potassium hydroxide.

After the hydrolysis, the reaction mixture is subjected to extraction with an appropriate organic solvent, and the organic solvent layer is distilled to give the desired 2-thiophene aldehyde, while the remaining thiophene is recovered. For the extraction, the same organic solvent as used in the above reaction or any other organic solvents immiscible with water can be employed.

According to the production process of the present invention, 2-thiophene aldehydes can be produced at high yield with excellent selectivity for the position of substituent groups, with no use of phosphorous oxychloride or pyridine.

EXAMPLES

The present invention will be further illustrated by way of the following examples, which are not to be construed to limit the scope thereof.

EXAMPLE 1

In a glass reaction vessel equipped with a gas inlet tube, a reflux condenser, a thermometer, and a stirrer, there were placed thiophene (25.3 g, 0.30 mol), N,N-dimethylformamide (28.5 g, 0.39 mol), and 1,2-dichloroethane (100.6 g). While the mixture was stirred, phosgene (38.6 g, 0.39 mol) was introduced into the mixture at 70° C. for 2 hours. The reaction mixture was kept warm at 70° C., and the reaction was stopped by the addition of water (50 g) when the conversion of thiophene reached 95%. While being cooled to 10° C. to 20° C., the reaction mixture was adjusted to pH7–8 by the addition of 15% aqueous sodium hydroxide. Then, the reaction mixture was separated into an organic layer and a water layer with a separatory funnel.

The water layer was extracted twice with 1,2-dichloroethane (50 g×2), and the 1,2-dichloroethane layers thus obtained were added to the above organic layer. The combined organic layer was washed twice with water (50 g×2), after which 1,2-dichloroethane and the remaining thiophene (1.27 g) were removed from the organic layer by distillation under ordinary pressure. The residual oil was distilled, and the distillates obtained at a boiling point of 91° C./33 hPa to 92° C./33 hPa were collected to give the desired 2-thiophene aldehyde (31.3 g). The percent yield of 2-thiophene aldehyde to converted thiophene was 98%.

The recovered 1,2-dichloroethane and the remaining thiophene were recycled for the formylation in another production stage.

EXAMPLES 2 and 3

In these examples, it was examined whether the reaction temperature affected the yield of 2-thiophene aldehydes or not. The reaction was performed in the same manner as described in Example 1, except that different temperatures were employed when phosgene was introduced and the reaction mixture was kept warm. The results are also shown in Table 1.

TABLE 1

| Example No. | Reaction temperature (°C.) | Yield[1] (g) | Yield[1] (mol) | Percent yield[2] (%) |
|---|---|---|---|---|
| 1 | 70–71 | 31.3 | 0.279 | 98 |
| 2 | 60–61 | 20.2 | 0.180 | 75 |
| 3 | 80–82 | 24.2 | 0.216 | 90 |

[1] Amount of obtained 2-thiophene aldehyde.
[2] Ratio of obtained 2-thiophene aldehyde to converted thiophene.

EXAMPLE 4

In a glass reaction vessel equipped with a gas inlet tube, a reflux condenser, a thermometer, and a stirrer, there were placed 2-methylthiophene (29.5 g, 0.30 mol), N,N-dimethylformamide (28.5 g, 0.39 mol), and 1,2-dichloroethane (100.6 g). While the mixture was stirred, phosgene (38.6 g, 0.39 mol) was introduced into the mixture at 60° C. for 2 hours. The reaction mixture was kept warm at 60° C. for 3 hours, and the reaction was stopped by the addition of water (50 g) when 2-methylthiophene as the starting material disappeared. While being cooled to 10° C. to 20° C., the reaction mixture was adjusted to pH7–8 by the addition of 15% aqueous sodium hydroxide. Then, the reaction mixture was separated into an organic layer and a water layer with a separatory funnel.

The water layer was extracted twice with 1,2-dichloroethane (50 g×2), and the 1,2-dichloroethane layers thus obtained were added to the above organic layer. The combined organic layer was washed twice with water (50 g×2), and 1,2-dichloroethane was removed from the organic layer by distillation under ordinary pressure. The residual oil was distilled, and the distillates obtained at a boiling point of 81° C./8 hPa to 82° C./8 hPa were collected to give 5-methyl-2-thiophene aldehyde (35.7 g). The percent yield of 5-methyl-2-thiophene aldehyde was 95%.

EXAMPLE 5

The reaction and the post-treatment were performed in the same manner as described in Example 4, except that 3-methylthiophene was used in place of 2-methylthiophene to give a distillate of 3-methyl-2-thiophene aldehyde (33.6 g; boiling b.p., 83° C./7 hPa to 85° C./7 hPa). The percent yield of 3-methyl-2-thiophene aldehyde was 90%.

What is claimed is:

1. A process for the production of a 2-thiophene aldehyde, comprising formylating thiophene or a thiophene derivative having a lower alkyl group or a halogen atom at a position selected from the 2- and 3- positions of the thiophene ring with a formamide and phosgene.

2. A process, according to claim 1 wherein said formamide is N,N-dimethylformamide.

3. The process according to claim 1, wherein said formylating is performed at a temperature of 40° C. to 90° C.

UNITED STATES PATENT AND TRADEMARK OFFICE
CERTIFICATE OF CORRECTION

PATENT NO. : 5,412,106
DATED : May 2 1995
INVENTOR(S) : YAMASHITA K. et al.

It is certified that error appears in the above-indentified patent and that said Letters Patent is hereby corrected as shown below:

ON THE COVER:

in item [73], line 2, please change "Sumitomo Seika Chemicals Co.," to read --Sumitomo Seika Chemicals Co., Ltd.--.

Signed and Sealed this

Tenth Day of October, 1995

*Attest:*

BRUCE LEHMAN

*Attesting Officer*     *Commissioner of Patents and Trademarks*